(12) United States Patent
Simard

(10) Patent No.: US 11,932,688 B2
(45) Date of Patent: Mar. 19, 2024

(54) TREATMENT FOR NEOPLASTIC DISEASES

(71) Applicant: Janssen Biotech, Inc., Horsham, PA (US)

(72) Inventor: John Simard, Austin, TX (US)

(73) Assignee: XBiotech Inc., Vancouver (CA)

(*) Notice: Subject to any disclaimer, the term of this patent is extended or adjusted under 35 U.S.C. 154(b) by 487 days.

(21) Appl. No.: 16/228,060

(22) Filed: Dec. 20, 2018

(65) Prior Publication Data

US 2019/0127460 A1    May 2, 2019

Related U.S. Application Data

(63) Continuation of application No. 13/215,464, filed on Aug. 23, 2011, now Pat. No. 10,294,296.

(60) Provisional application No. 61/480,635, filed on Apr. 29, 2011, provisional application No. 61/411,183, filed on Nov. 8, 2010, provisional application No. 61/406,759, filed on Oct. 26, 2010, provisional application No. 61/376,097, filed on Aug. 23, 2010.

(51) Int. Cl.
*A61K 39/395* (2006.01)
*C07K 16/24* (2006.01)
*A61K 39/00* (2006.01)

(52) U.S. Cl.
CPC ...... *C07K 16/245* (2013.01); *A61K 2039/505* (2013.01); *C07K 2317/76* (2013.01)

(58) Field of Classification Search
None
See application file for complete search history.

(56) References Cited

U.S. PATENT DOCUMENTS

| | | |
|---|---|---|
| 4,634,664 A | 1/1987 | Oestberg |
| 4,965,198 A | 10/1990 | Yamasaki |
| 4,968,607 A | 11/1990 | Dower |
| 5,034,316 A | 7/1991 | Weisbart |
| 5,168,062 A | 12/1992 | Stinski |
| 5,231,024 A | 7/1993 | Moeller |
| 5,530,101 A | 6/1996 | Queen |
| 5,585,089 A | 12/1996 | Queen |
| 5,654,407 A | 8/1997 | Boyle |
| 5,693,762 A | 12/1997 | Queen |
| 5,792,838 A | 8/1998 | Smith |
| 5,795,967 A | 8/1998 | Aggarwal |
| 5,932,188 A | 8/1999 | Snow |
| 5,959,085 A | 9/1999 | Garrone et al. |
| 6,090,382 A | 7/2000 | Salfeld |
| 6,140,470 A | 10/2000 | Garen |
| 6,623,736 B2 | 9/2003 | Tobinick |
| 7,105,183 B2 | 9/2006 | McGrath |
| 7,718,674 B2 | 5/2010 | Aberg |
| 8,034,337 B2 | 10/2011 | Simard |
| 8,034,377 B2 | 10/2011 | Brune |
| 8,242,074 B2 | 8/2012 | Simard |
| 8,388,956 B2 | 3/2013 | Simard |
| 8,388,969 B2 | 3/2013 | Simard |
| 8,398,966 B2 | 3/2013 | Wu |
| 8,546,331 B2 | 10/2013 | Simard |
| 8,679,489 B2 | 3/2014 | Simard |
| 8,697,689 B2 | 4/2014 | Cid-Nunez |
| 8,784,817 B2 | 7/2014 | Simard |
| 9,181,338 B2 | 11/2015 | Simard |
| 9,416,172 B2 | 8/2016 | Simard |
| 9,840,558 B2 | 12/2017 | Simard |
| 10,294,296 B2 | 5/2019 | Simard |
| 10,899,833 B2 | 1/2021 | Simard |
| 2002/0022720 A1 | 2/2002 | Le |
| 2002/0044919 A1 | 4/2002 | Yu |
| 2003/0004061 A1 | 1/2003 | Kraemer |
| 2003/0023205 A1 | 1/2003 | Botich |
| 2003/0026806 A1 | 2/2003 | Witte et al. |
| 2003/0040617 A9 | 2/2003 | Rosen |
| 2003/0175832 A1 | 9/2003 | Marton |
| 2003/0232054 A1 | 12/2003 | Tang |
| 2004/0097712 A1 | 5/2004 | Varnum |
| 2004/0185514 A1 | 9/2004 | Frostegard |
| 2004/0224893 A1 | 11/2004 | Wang |
| 2005/0005401 A1 | 1/2005 | Bae |
| 2005/0054019 A1 | 3/2005 | Michaud |
| 2005/0129699 A1 | 6/2005 | Salcedo |
| 2005/0147603 A1 | 7/2005 | Smith |
| 2005/0276807 A1 | 12/2005 | Skurkovich |
| 2006/0127407 A1 | 6/2006 | Chen |
| 2006/0159775 A1 | 7/2006 | McGrath |
| 2007/0071675 A1 | 3/2007 | Wu |
| 2008/0050310 A1 | 2/2008 | Ebens, Jr. et al. |
| 2009/0123415 A1 | 5/2009 | Simard |
| 2009/0191149 A1 | 7/2009 | Simard |
| 2009/0215992 A1 | 8/2009 | Wu |
| 2009/0258070 A1 | 10/2009 | Burnier |

(Continued)

FOREIGN PATENT DOCUMENTS

| | | |
|---|---|---|
| AU | 2007202323 | 6/2007 |
| CA | 2426384 | 4/2003 |

(Continued)

OTHER PUBLICATIONS

Hanna et al. (2006) J. Clin. Oncol. 24: 5253-5258.*
Kurzrock et al., OncoImmunology Journal, 2019, vol. 8, No. 3, pp. 1-7.
Garrone P et al, Generation and characterization of a human monoclonal autoantibody that acts as a high affinity interleukin-1 alpha specific inhibitor, Molecular Immunology, Pergamon, vol. 33, No. 7-8, pp. 649-658.
Wood D D et al, "Release of Interleukin-1 From Human Synovial Tissue In-Vitro", Arthritis and Rheumatism, vol. 28, No. 8, pp. 853-862.

(Continued)

*Primary Examiner* — Michael D Pak
(74) *Attorney, Agent, or Firm* — Stanley A. Kim

(57) ABSTRACT

Administration of a mAb that specifically binds IL-1α is useful for treating tumor-associated diseases in human subjects.

12 Claims, No Drawings

(56) References Cited

U.S. PATENT DOCUMENTS

| | | |
|---|---|---|
| 2009/0291081 A1 | 11/2009 | Hsieh |
| 2009/0298096 A1 | 12/2009 | Simard |
| 2010/0040574 A1 | 2/2010 | Simard |
| 2010/0047239 A1 | 2/2010 | Wu |
| 2010/0068212 A1 | 3/2010 | Simard |
| 2010/0221179 A1 | 9/2010 | Hsieh |
| 2011/0008282 A1 | 1/2011 | Simard |
| 2011/0142761 A1 | 6/2011 | Wu |
| 2011/0311547 A1 | 12/2011 | Simard |
| 2012/0015384 A1 | 1/2012 | Simard |
| 2012/0045444 A1 | 2/2012 | Simard |
| 2012/0231012 A1 | 9/2012 | Simard |
| 2012/0251548 A1 | 10/2012 | Simard |
| 2012/0275996 A1 | 11/2012 | Hsieh |
| 2013/0039921 A1 | 2/2013 | Simard |
| 2013/0078258 A1 | 3/2013 | Simard |
| 2013/0195877 A1 | 8/2013 | Simard |
| 2013/0287788 A1 | 10/2013 | Simard |
| 2014/0086933 A1 | 3/2014 | Simard |
| 2015/0024031 A1 | 1/2015 | Rabinow |
| 2016/0024190 A1 | 1/2016 | Ohsawa |

FOREIGN PATENT DOCUMENTS

| | | |
|---|---|---|
| CN | 1431909 A | 7/2003 |
| CN | 1662557 | 8/2005 |
| EP | 0267611 | 5/1988 |
| EP | 0659766 | 6/1995 |
| JP | 2004285057 | 10/2004 |
| JP | 2006-502698 A | 1/2006 |
| JP | 2007-211022 A | 8/2007 |
| JP | 2009-022273 A | 2/2009 |
| JP | 2009-537628 A | 10/2009 |
| WO | 9006371 | 6/1990 |
| WO | 1990011091 | 10/1990 |
| WO | 9524917 A1 | 9/1995 |
| WO | 9635719 | 11/1996 |
| WO | 0120828 | 3/2001 |
| WO | 0233094 | 4/2002 |
| WO | 02082041 A2 | 10/2002 |
| WO | 03074566 A2 | 9/2003 |
| WO | 2004100987 | 11/2004 |
| WO | 2005003175 A2 | 1/2005 |
| WO | 2006001967 | 1/2006 |
| WO | 2007015128 | 2/2007 |
| WO | 2007039552 | 4/2007 |
| WO | 2007120828 | 10/2007 |
| WO | 2007132338 | 11/2007 |
| WO | 2007135546 | 11/2007 |
| WO | 2007135546 A2 | 11/2007 |
| WO | 2009148575 A1 | 12/2009 |
| WO | 2010030979 | 3/2010 |
| WO | 2010087972 | 8/2010 |
| WO | 2011153477 | 12/2011 |
| WO | 2011159976 | 12/2011 |
| WO | 2012027324 | 3/2012 |
| WO | 2012034039 | 3/2012 |
| WO | 2012135812 | 10/2012 |
| WO | 2013043973 | 3/2013 |
| WO | 2014055541 | 4/2014 |
| WO | 2014055544 | 4/2014 |
| WO | 2018150265 | 8/2018 |

OTHER PUBLICATIONS

Vazquez A et al, "Interleukin 1 can replace monocytes for the specific human B-cell response to a particulate antigen", Cellular Immunology, Academic Press, San Diego, CA, US, vol. 86, No. 2, pp. 287-298.

Jefferis Roy, "Antibody therapeutics: isotype and glycoformselection", Expert Opinion on Biological Therapy, vol. 7, No. 9, ISSN 1471-2598, pp. 1401-1413.

Salfeld Jochen G, "Isotype selection in antibody engineering.", Nature Biotechnology, vol. 25, No. 12, ISSN 1546-1696, pp. 1369-1372.

Niki, Y, et al. Membrane-associated IL-1 contributes to chronic synovitis and cartilage destruction in human IL-1 alpha transgenic mice. J. Immunology, 2004, vol. 172, No. 1, p. 577-584.

GenBank, Database accession No. AY510107.1 DOI: https://www.ncbi.nlm.nih.gov/nuccore/AY510107.1.

Svenson, M. et al., Binding of Cytokines to Pharmaceutically Prepared Human Immunoglobulin, J. Clin. Invest., Nov. 1993, vol. 92:2533-2539.

Chang, C.H. et al., "Interleukin-1alpha released from epithelial cells after adenovirus type 37 infection activates intercellular adhesion molecule 1 expression on human vascular endothelial cells," Journal of Virology, Jan. 2002, vol. 76, No. 1:427-431.

Barkley, D.E.H. et al: "Cells with dendritic morphology and bright interleukin-1alpha staining circulate in the blood of patients with rheumatoid arthritis," Clin.Exp.Immmunol., 1990, vol. 80:25-31.

Yanni, G et al: "Intramuscular gold decreases cytokine expression and macrophage numbers in the rheumatoid synovial membrane," Annals of the Rheumatic Diseases, 1994, vol. 53:315-322.

Dekker, S.K. et al: "Characterization of interleukin-1 alpha-induced melanoma cell motility: inhibition by type I and type II receptor-blocking monoclonal antibodies," Melanoma Research, 1997, vol. 7:223-230.

Kleiman, et al: "Invasion assays," Current Protocols in Cell Biology, 2001, 12.2.1-12.2.5.

Sawai, H. et al: "Interleukin-1 alpha enhances the aggressive behavior of pancreatic cancer cells by regulating the alpha 6 beta 1-integrin and urokinase plasminogen activator receptor expression," MC Cell Biology, 2006:1-13.

Li, X. et al: "Interleukin-1alpha up-regulation in vivo by a potent carcinogen 7, 12-Dimethylbenz(a)anthracene (DMB) and control of DMBA-induced inflammatory responses," Cancer Res, 2002, vol. 62:417-423.

Nozaki, S. et al: "Cancer Cell-Derived Interleukin 1 alpha contributes to autocrine and paracrine induction of pro-metastatic genes in breast cancer," Biochemical and Biophysical Research Communications, 2000, vol. 275:60-62.

Voronov, E. et al: "IL-1 is required for tumor invasiveness and angiogenesis," PNAS, 2003, vol. 100, No. 5:2645-2650.

Uefuji, K. et al: "Increased expression of interleukin-1alpha and cyclooxygenase-2 in human gastric cancer: a possible role in tumor progression," 2005, Anticancer Research, vol. 25:3225-3230.

Shreeniwas, R. et al: "Hypoxia-mediated induction of endothelial cell interleukin-1alpha: an autocrine mechanism promoting expression of leukocyte adhesion molecules on the vessel surface," 1992, J. Clin. Invest., vol. 90:2333-2339.

Bendtzen, Klaus et al., High-Avidity Autoantibodies to Cytokines, Trends Immunology Today, May 1998, vol. 19, No. 5 209, 3 pages.

Bendtzen, Klaus et al., Detection of Autoantibodies to Cytokines, Molecular Biotechnology, 2000, vol. 14, 14 pages.

Dardik, Alan et al., Shear stress-stimulated endothelial cells induce smooth muscle cell chemotaxis via platelet-derived growth factor-BB and interleukin-1alpha, Journal of Vascular Surgergy, Feb. 2005, vol. 41:321-331.

Dinarello, Charles A., Modalities for reducing interleukin 1 activity in disease, TiPS, May 1993 vol. 14:155-159.

Dinarello, Charles A. et al., Anticytokine strategies in the treatment of the systemic inflammatory response syndrome, The Journal of the American Medical Association, Apr. 1993, vol. 269, No. 14:1829-1835.

Dinarello, Charles A., Biologic basis for interleukin-1 in disease, Blood, Mar. 1996, vol. 87, No. 6:2095-2147.

Dinarello, Charles A., Therapeutic strategies to reduce IL-1 activity in treating local and system inflammation, Current Opinion in Pharmacology, 2004, vol. 4:378-385.

Larrick, James W. et al., Prospects for the therapeutic use of human monoclonal antibodies, Journal of Biological Response Modifiers, 1986, vol. 5:379-393.

Griffiths, Andrew D. et al., Human anti-self antibodies with high specificity from phage display libraries, the EMBO Journal, 1993, vol. 12, No. 2:725-734.

(56) References Cited

OTHER PUBLICATIONS

Satoh, H. et al., Characterization of anti-IL-1alpha autoantibodies in the sera from healthy humans, Immunopharmacology, 1994, vol. 27:107-118.
Hansen, M. B. et al., Sex- and age-dependency of IgG autoantibodies against IL-1 alpha in healthy humans, European Journal of Clinical Investigation, 1994, vol. 24:212:218.
Jouvenne, P. et al., High levels of neutralizing autoantibodies against IL-1 alpha are associated with a better prognosis in chronic polyarthritis: a follow-up study, Scand. J. Immunol., 1997, vol. 46:413-418.
Lindqvist, E. et al., Prognostic laboratory markers of joint damage in rheumatoid arthritis, Ann Rheum Dis, 2005, vol. 64:196-201.
Ogushi, F. et al., Autoantibodies to IL-1alpha in sera from rapidly progressive idiopathic pulmonary fibrosis, The Journal of Medical Investigation, 2001, vol. 48:181-189.
Ross, Christian, et al., High avidity IFN-neutralizing antibodies in pharmaceutically prepared human IgG, J. Clin. Invest., May 1995, vol. 95:1974-1978.
Saurat, Jean-Hilaire, et al., Anti-interleukin-1alpoha autoantibodies in humans: Characterization, isotype distribution, and receptor-binding inhibition—Higher frequency in Schnitzler's syndrome (urticaria and macroglobulinemia), J. Allergy Clin. Immunol., Aug. 1991, vol. 88, No. 2:243-256.
Suzuki, Hiroshi et al., Demonstration of Neutralizing Autoantibodies against II-1 alpha IN sera from patients with rheumatoid arthritis, The Journal of Immunology, Oct. 1, 1990, vol. 145, No. 7:2140-2146.
Svenson, M. et al., IgG Autoantibodies against Interleuking 1alpha in sera of normal individuals, Scand. J. Immunol., 1989, vol. 29:489-492.
Svenson, M. et al., Effects of human anti-IL-1alpha autoantibodies on receptor binding and biological activities of IL-1 alpha, Cytokine, Mar. 1992, vol. 4, No. 2:125-133.
Svenson, M. et al., Distribution and characterization of autoantibodies to interleukin 1 alpha in normal human sera, Scand. J. Immunol., 1990, vol. 32:695-701.
Svenson, M. et al., Antibody to granulocyte-macrophage colony-stimulating factor is a dominant anticytokine activity in human IgG preparations, Blood, Mar. 1998, vol. 91, No. 6:2054-2061.
Svenson M, et al. Cytokine vaccination: neutralising IL-1alpha autoantibodies induced by immunisiation with homologous IL-1alpha. Journal of Immunological Methods, 2000, vol. 236, No. 1-2, p. 1-8.
Waehre et al., Increased expression of interleukin-1 in coronary artery disease with downregulatory effects of HMG-CoA reductase inhibitors, «circ.ahajournals.org», downloaded on Jan. 15, 2008:1966-1972.
Clinton Steven K. et al., Interleukin-1 gene expression in rabbit vascular tissue in vivo, American Journal of Pathology, Apr. 1991, vol. 138, No. 4:1005-1014.
Von Der Thusen, Jan H., et al., Interleukins in atherosclerosis: Molecular pathways and therapeutic potential, Pharmacol Rev, 2003, vol. 55, No. 1:133-166.
Kasahara, T. et al., Preparation and characterization of polyclonal and monoclonal antibodies against human interleukin 1 alpha (IL 1alpha), The Journal of Immunology, Mar. 1987, vol. 138, No. 6:1804-1812.
Merhi-Soussi, F. et al., Interleukin-1 plays a major role in vascular inflammation and atherosclerosis in male apolipoprotein E-knockout mice, Cardiovacular Research, 2006, vol. 66:583-593.
Ross, C. et al., Increased in vivo antibody activity against interferon alpha, interleuking-1alpha, and interleukin-6 after high-dose lg therapy, Blood, Sep. 1997, vol. 90, No. 6:2376-2380.
Ito, R. et al., Interleukin 1 alpha acts as an autocrine growth stimulator for human gastric carcinoma cells, Cancer Research, Sep. 1993, vol. 53:4102-4106.
Shirakawa, F. et al., Autocrine stimulation of interleukin 1 alpha in the growth of adult human T-cell leukemia cells, Cancer Research, Mar. 1989, vol. 49:1143-1147.

Apte, Ron N., et al., Effects of micro-environment- and malignant cell-derived interleukin-1 in carcinogenesis, tumour invasiveness and tumour-host interactions, European Journal of Cancer, 2006, vol. 42:751-759.
Dinarello, Charles A., The role of interleukin-1 in disease, The New England Journal of Medicine, 1993, vol. 328, No. 2:106-113.
Wake, R. et al., Gender differences in ischemic heart disease, Recent Patents on Cardiovascular Drug Discovery, 2009, vol. 4:234-240.
Mariotti, Massimo et al., Iterleukin 1 alpha is a marker of endothelial cellular senescent, Immunity & Ageing, Research, Apr. 2006, vol. 3, No. 4:1-6.
McHale, Julie F. et al., TNF-alpha and IL-sequentially induce endothelial ICAM-1 and VCAM-1 expression in MRL/lpr lupus-prone mice, The American Association of Immunologists, 1999, vol. 163:3993-4000.
Sandborg, Christy L. et al., Modulation of IL-1alpha, IL-1beta, and 25K Mr Non-IL-1 activity released by human mononuclear cells, Journal of Leukocyte Biology, 1989, vol. 46:417-427.
GenBank entry AY510107.1, *Homo sapiens* 9F11 monoclonal IgM antibody light chain mRNA, complete cds, 2005 (retrieved from the Internet on Apr. 23, 2010, <http://www.ncbi.nlm.nih.gov/nuccore/41388185>, 1 page.
Sunahara, N. et al., Differential determination of recombinant hum interleukin-1 alpha and its deamidated derivative by two sandwhich enzyme immunoassays using monoclonal antibodies. Comparison with a polyclonal antibody-based competitive enzyme immunoassay., J Immunol Methods, 1989, vol. 119:75-82 (Abstract only).
Miossec, P., Anti-interleukin 1 alpha autoantibodies, Ann Rheum Dis, 2002, vol. 61:577-579.
Horai, R. et al., Production of mice deficient in genes for interleukin (IL)-1alpha, IL-1beta, IL-1alpha/beta, and IL-1 receptor antagonist shows that IL-1beta is crucial in turpentine-induced fever development and glucocorticoid secretion, J. Exp. Med, 1998, vol. 187, No. 9:1463-1475.
Kanai, T. et al., Extracorporeal elimination of TNF-alpha-producing CD14 dull CD16+ monocytes in leukocytapheresis therapy for ulcerative colitis, Inflamm Bowel Dis, Mar. 2007, vol. 13, No. 3:284-290.
Braddock, M. et al., Therapeutic potential of targeting IL-1 and IL-18 in inflammation, Expert Opin. Biol. Ther., 2004, vol. 4, No. 6:8476-860.
Eugui, E.M. et al., Antibodies against membrane interleukin 1alpha activate accessory cells to stimulate proliferation of T lymphocytes, Proc. Natl. Acad. Sci USA, 1990, vol. 87:1305-1309.
Janeway, C.A., Jr. et al, The induction, measurement, and manipulation of the immune response, ImmunoBiology, the Immune System in Health and Disease, 1997, Third Edition, 8 pages.
Kaji, Mitsuhito et al, E-selectin expression induced by pancreas-carcinoma-derived interleukin-1alpha results in enhanced adhesion of pancreas-carcinoma cells to endothelial cells, Intl Journal of Cancer, 1995, vol. 60, Issue 5:712-717.
Jefferis, Roy: "Antibody therapeutics: isotype and glycoform selection," Expert Opin. Biol. Ther. (2007) 7 (9):1401-1413.
Pascual, V. et al: "Role of interleukin-1 (IL-1) in the pathogenesis of systemic onset juvenile idiopathic arthritis and clinical response to IL-1 blockade," The Journal of Experimental Medicine (2005), vol. 201, No. 9:1479-1486.
Buchan, G. et al: "Interleukin-1 and tumour necrosis factor mRNA expression in rheumatoid arthritis: prolonged production of IL-1 alpha," Clin. Exp. Immunol. (1988), vol. 73:449-455.
Hata, H. et al: "Distinct contribution of IL-6, TNF-alpha, IL-1, and IL-10 to T cell-mediated spontaneous autoimmune arthritis in mice," The Journal of Clinical Investigation (2004), vol. 114, No. 4: 582-588.
Chen, Z. et al: "Effects of interleukin-1alpha, interleukin-1 receptor antagonist, and neutralizing antibody on proinflammatory cytokine expression by human squamous cell carcinoma lines," Cancer Research (1998), vol. 58:3668-3676.
Fukumoto, Y. et al., Inflammatory Cytokines Cause Coronary Arteriosclerosis-Like Changes and Alterations in the Smooth-Muscle Phenotypes in Pigs, Journal of Cardiovascular Pharmacology, 1997, vol. 29:222-231.

(56) References Cited

OTHER PUBLICATIONS

Chamberlain, R.S. et al., Innovations and strategies for the development of anticancer vaccines, Exp. Opin. Pharmacother., 2000, vol. 1(4)603-614.

Janik, John E. et al: "Interleukin 1 alpha increases serum leptin concentrations in humans," Journal of Clinical Endocrinology and Metabolism, vol. 92, No. 9, 1997: 3084-3086.

Kurokawa, Ichiro et al: "New developments in our understanding of acne pathogenesis and treatment," Experimental Dermatology, vol. 18, 2009:821-832.

Lubberts, Erik, et al: "Treatment with a neutralizing anti-murine inerleukin-17 antibody after the onset of collagen-induced arthritis reduces joint inflammation, cartilage destruction, and bone erosion," Arthritis & Rheumatism, vol. 50, No. 2, Feb. 2004:650-659.

Oriuchi, Noboru et al: "Current status of cancer therapy with radiolabeled monoclonal antibody," Annals of Nuclear Medicine, vol. 19, No. 5, 2005:355-365.

Boselli, Joseph et al: Fibronectin: Its relationshp to basement membranes, Light Microscopic Studies, Cell.Res., vol. 5, 1981:391-404.

Hoge, E.A. et al: "Broad spectrum of cytokine abnormalities in panic disorder and posttraumatic stress disorder," Depression and Anxiety, vol. 26, No. 5, May 2009:447-455; Abstract only.

Mach, Francois: "Toward new therapeutic strategies against neointimal formation in restenosis," Arterioscler Thromb Vasc Biol, vol. 20, 2000:1699-1700.

Morton, Allison, C. et al: "Interleukin-1 receptor antagonist alters the response to vessel wall injury in a porcine coronary artery model," Cardiovascular Research, vol. 68, 2005: 493-501.

Heyderman, R.S. et al: "Modulation of the endothelial procoagulant response to lipoploysaccharide and tumour necrosis factor-alpha in-vitro: The effects of dexamethasone, pentoxifylline, iloprost and a polyclonal anti-human IL-1alpha antibody," Inflamm Res, vol. 44, 1995:275-280.

Joosten, M. et al: "Amelioration of established collagen-induced arthritis (CIA) with anti-IL-1," Agents Actions. vol. 41, Special Conference Issue, 1994:C174-C176.

U.S. National Institutes of Health: "Safety and Preliminary Efficacy Study of an Anti-inflammatory Therapeutic Antibody in Reducing Restenosis," NCT01270945, ClinicalTrials.gov, Jan. 4, 2011, 3 pages.

Xbiotech, Inc. Pressrelease: "XBiotech Files Investigational New Drug (IND) Application with the FDA for the treatment of Chronic Myelogenous Leukemia," Evaluate, Nov. 22, 2010, 2 pages.

Rhim, JH, et al.: "Cancer cell-derived IL-1 alpha induces Il-8 release in endothelial cells," J Cancer Res Clin Oncol, Jan. 2008, vol. 134(1):45-50. Epub Jul. 11, 2007; (Abstract only).

Sakurai, T. et al.: "Hepatocyte Necrosis Induced by Oxidative Stress and IL-1alpha Release Mediate Carcinogen-Induced Compensatory Proliferation and Liver Tumorigenesis," Cancer Cell, Aug. 12, 2008, vol. 14:156-165.

Mizutani, H.: "Endogenous neutralizing anti-Il-1alpha antibodies in inflammatory skin diseases: possible natural inhibitor for over expressed epidermal IL-1," 1999, Journal of Dermatological Science, vol. 20:63-71.

Zhu, Y. et al., "The clinical study about interleukin-1 and tumor necrosis factor alpha in hepatocirrhosis," Chinese Journal of Clinical Hepatology, 2001, vol. 17, Issue 4: 233-234.

Skrzeczynska, J. et al., "CD14+CD16+ Monocytes in the Course of Sepsis in Neonates and Small Children: Monitoring and Functional Studies," Scandinavian Journal of Immunology, 2002, vol. 55:629-638.

Grahame, V. et al: "The Psychological Correlates of Treatment Efficacy in Acne," Dermatol Psychosom, 2002, vol. 3:119-125.

Murota, H. et al., "Exacerbating factors of itch in atopic dermatitis," Allergology International, 2017, No. 66:8-13.

Fenini, G. et al., "Potential of IL-1, IL-18 and Inflammasome Inhibition for the Treatment of Inflammatory Skin Diseases," Frontiers in Pharmacology, May 2017, vol. 8:1-20.

Carrasco, Daniel et al: "An Open Label, Phase 2 Study of MABp1 Monotherapy for the Treatment of Acne Vulgaris and Psychiatric Comorbidity," Journal of Drugs in Dermatology, Jun. 2015, vol. 14, Issue 6: 560-564.

Rubinow, David R. et al: "Reduce anxiety and depression in cystic acne patients after successful treatment with oral isotretinoin," Journal of the American Academy of Dermatology, 1987, vol. 17, No. 1:25-32.

Kaymak, Yesim et al: "Comparison of depression, anxiety and life quality in acne vulgaris patients who were treated with either isotretinoin or topical agents, The International Society of Dermatology," 2009, vol. 48:41-46.

Dinarello, Charles A. et al: "Treating inflammation by blocking interleukin-1 in a broad spectrum of diseases," Nature Reviews/ Drug Discovery, Aug. 2012, vol. 11: 633-652.

Rossi, Silvia et al.: "Interleukin-1 beta causes anxiety by interacting with the endocannabinoid system," The Journal of Nleuroscience, Oct. 3, 2012, vol. 32, No. 40:13896-13905.

Szabo, K. et al: "Interleukin-1A +4845(G>T) polymorphism is a factor predisposing to acne vulgaris," Tissue Antigens, 2010, vol. 76:411-415.

Bonifati, C. et al.: "IL-lalpha, IL-1beta and psoriasis: conflicting results in the literature. Opposite behaviour of the two cytokines in lesional or non-lesional extracts of whole skin," Journal of Biological Regulators and Homeostatic Agents, Oct. 1997, vol. 11, No. 4:133-136.

Gonzalez-Lopez, M.A. et al: "New-onset psoriasis following treatment with the interleukin-1 receptor antagonist anakinra," British Journal of Dermatology, May 2008, vol. 158, No. 5:1146-1148.

Yost, J. and J.E. Gudjonsson: "The role of TNF inhibitors in psoriasis therapy: new implications for associated comorbidities," Medicine Reports, May 2009, vol. 1, No. 30:1-4.

Kanni, Theodora, et al.: "MABp1 Targeting IL-1 alpha for moderate to severe hidradenitis suppurativa not eligible for adalimumab: A randomized study," Journal of Investigative Dermatology, 2018, vol. 138:795-801.

Riis, Peter Theut et al.: "Investigational drugs in clinical trials for hidradenitis suppurativa," Expert Opinion on Investigational Drugs, 2018, vol. 27, No. 1:43-53.

Rectenwald et al., "Direct Evidence for Cytokine Involvement in Neointimal Hyperplasia,"; Circulation, vol. 102, pp. 1697-1702, Oct. 3, 2000.

Kamari et al., BBRC: 405, pp. 197-203 (Year: 2011), 7 pages.
Waehreetal., Circulation: 109, pp. 1966-1972 (Year: 2004).
Moyeretal., Am. J. Pathol.:138, pp. 951-960 (Year: 1991).
Larionov et al., Acta Neuropathol: 113, pp. 33-43 (Year: 2007).
Zaragoza et al. (2011), J. of Biomedicine and Biotechnology, vol. 2011, p. 1-13.
Patti et al., Am. J. Cardiol: 89., pp. 372-376 (Year: 2002).
Beasley, Debbie and Angela L. Cooper: "Constitutive expression of interleukin-1 alpha precursor promotes human vascular smooth muscle cell proliferation," American Physiological Society, 1999, No. 276:H901-H912.

Morton et al. Crdiovascular Research, vol. 68, pp. 401-501 (Year: 2005).

Xbiotch IND for the treatment of Chronic Myelogenous Leukemia, p. 1 (Year: 2010).

Mandinov, L. et al.: "Inhibition of in-stent restenosis by oral copper chelation in porcine coronary arteries," Am J Physiol Heart Circ Physiol, 2006, vol. 291:H2692-H2697.

Giamarellos-Bourboulis, EvangelosJ. MABpi In Hidradenitis Suppurativa Refractory to Adalimumab, ClinicalTrials.gov, Identifier: NCT02643654, 19 pages (Dec. 31, 2015). (Year: 2015).

Kimball et al. Assessing the validity, responsiveness and meaningfulness of the Hidradenitis Suppurativa Clinical Response (HiSCR ) as the clinical endpoint for hidradenitis suppurativa treatment. British Journal of Dermatology vol. 171:1434-1442 (2014). (Year: 2014).

Martin-Ezquerra et al. Use of biological treatments in patients with hidradenitis suppurativa. Giornale Italiano di Dermatologia e Venereologia. Journal on Dermatology and Sexually Transmitted Diseases. vol. 152(4):373-8, Aug. 2017. Article first published online Dec. 16, 2016. (Year: 2017).

(56) References Cited

OTHER PUBLICATIONS

Kelekis, N.L et al., "Ultrasound aids and diagnosis and severity assessment of hidradenitis suppurativa", British Journal of Dermatology, 2010, vol. 162, Issue 6, pp. 1395-1416.
International Search Report issued in corresponding international patent application No. PCT/IB2018/000209 dated Jul. 5, 2018; 4 pages.
Immunobiology, Janeway et al., The immune system in health and disease, 3rd edition, 1997section 3.4 and figure 3.4, 9 pages.
Fujii, Masakazu et al.: "A case of advanced gastric cancer with carcinomatous ascites successfully treated with intraperitoneal administration of CDDP and TS-1," Japanese Journal of Gastoenterological Surgery, 2006, vol. 39:189-195.
Wang et al. Nuc. Acids Res. 1999, vol. 27, pp. 4609-4618.
Kaufman et al Blood, 1999, vol. 94, pp. 3178-3184.
Wigley et al. Reprod Fert Dev, 1994, vol. 6, pp. 585-588.
Campbell et al. Theriology, 1997, vol. 47, No. 1, pp. 63-72.
Kishore et al, Immunopharmacology, 2000, vol. 49, pp. 159-170.
Li et al, Cancer Research, 2002, vol. 62, pp. 417-423.
U.S. Appl. No. 13/162,705 (SIMARD) filed on Jun. 17, 2011, "Arthritis Treatment," not yet published; 18 pages.
U.S. Appl. No. 13/215,464 (SIMARD) filed on Aug. 23, 2011, "Treatment for Neoplastic Diseases," not yet published; 17 pages.
U.S. Appl. No. 13/224,975 (SIMARD) filed on Sep. 2, 2011, "Interleukin-1 Alpha Antibodies and Methods of Use," not yet published; 25 pages.
U.S. Appl. No. 13/225,029 (SIMARD) filed on Sep. 2, 2011, "Interleukin-1 Alpha Antibodies and Methods of Use," not yet published; 25 pages.
U.S. Appl. No. 13/225,004 (SIMARD) filed on Sep. 2, 2011, "Interleukin-1 Alpha Antibodies and Methods of Use," not yet published; 25 pages.
Eugui et al. (1990) PNAS 87: 1305-1309.
U.S. Appl. No. 13/224,913 (SIMARD) filed on Sep. 2, 2011, "Interleukin-1 Alpha Antibodies and Methods of Use," not yet published; 25 pages.
Amicon Ultra2001; Millipore technical datasheet; 9 pages.
GE Healthcare Instructions, 2005, 12 pages.
Kaji, M.: "E-selectin expression induced by pancreas-carcinoma-derived interleukin-1alpha results in enhanced adhesion of pancreas-carcinoma cells to endothelial cells," Mar. 1996, vol. 60Issue 5:712-717(Abstract).
Schlitt, Axel et al., CD14+D16+ monocytes in coronary artery disease and their relationship to serum TNF-alpha levels, Thromb Haemost, 2004, vol. 92:419-424.
Ziegler-Heitbrock, Loems, The CD14+CD16+ blood monocytes: their role in infection and inflammation, Journal of Leukocyte Biology, Mar. 2007, vol. 81:584-592.
Beige, Kai-Uwe et al., The Proinflammatory CD14+ CD16+DR++ Monocytes are a Major Source of TNF1, The Journal of Immunology, 2002, vol. 168:3536-3542.
Iwahashi, Mitsuhiro et al., Expression of Toll-Like Receptor 2 on CD16+ Blood Monocytes and Synovial Tissue Macrophages in Rheumatoid Arthritis, Arthritis and Rheumatism, 2004, vol. 50, No. 5:1457-1467.
Ulrich, C. et al., Proinflammatory CD14+CD16+ Monocytes are Associated with Subclinical Atherosclerosis in Renal Transplant Patients, American Journal of Transplantation, 2008, vol. 8:103-110.
Heine, GH., et al., CD14++CD16+ monocytes but not total monocyte numbers predict cardiovascular events in dialysis patients, Kidney International, 2008, vol. 73:622-629.
Joosten, Leo A.B. et al: "Anticytokine Treatment of Established Type II Collagen-Induced Arthritis in DBA/1 Mice," Arthritis & Rheumatism, May 1996, vol. 39, No. 5:797-809.
Saitta, P. et al: "An Update on the Presence of Psychiatric Comorbidities in Acne Patients, Part 2: Depression, Anxiety, and Suicide," CUTIS, Aug. 2011, vol. 88:92-97.
Marques-Deak, Andrea et al: "Measurement of cytokines in sweat patches and plasma in healthy women: Validation in a controlled study," Journal of Immunological Methods, vol. 315, 2006: 99-109.
Clinical Trial Review: "Acne," Journal of Drugs in Dermatology (JD online Today), Jun. 2012, vol. 11, Issue 6:1-3; «http://jddonline.eom/articles/dermatology/S1545961612P0780X/1», last visited on Jan. 17, 2017.
Yamada, Takayuki et al.: "Growth Dependency of a new human pancreatic cancer cell line, YAPC, on autocrine interleukin-1 alpha stimulation," Int. J. Cancer, 1998, vol. 76:141-147.
El-Osta, Hazem et al.: "Successful treatment of Castleman's Disease with Interleukin-1 receptor antagonist (Anakinra)," Molecular Cancer Therapy, 2010, vol. 9:1485-1488.
SIGMA Life Science: "Gel Filtration Chromatography," no date; Office Action of U.S. Appl. No. 13/225,029 dated Jun. 19, 2014, 6 pages.
Clinical Trial Review: Acne; «http://jddonline.eom/articles/dermatology/S1545961612P0780X/1», last visited on Oct. 16, 2014; 3 pages.
Stark et al., British Journal of Cancer, 83(10):1261-1267, 2000.
Feldman et al., American Family Physician, 69(9):2123-30, 2004.
Oldenburg, H.S.A., et al. Cachexia and the acute-phase protein response in inflammation are regulated by interleukin-6. Eur. J. Immunol., 1993, vol. 23, p. 1889-1894.
Hong, David S. et al: "MABp1, a first-in-class true human antibody targeting interleukin-1alpha in refractory cancers: an open-label, phase 1 dose-escalation and expansion study," Lancet Oncol, 2014, vol. 15:656-66.
Fong Y; Moldawer L L; Marano M; Wei H; Barber A; Manogue K; Tracey K J; Kuo G; Fischman D A; Cerami A; et al., "Cachectin/TNF or IL-1 alpha induces cachexia with redistribution of body proteins.", American Journal of Physiology, American Physiological Society, US, US, (Mar. 1, 1989), vol. 256, No. 3, ISSN 0002-9513, pp. R659-R665, XP009184008.
Hong, David S. et al.: "Abstract A211: A phase I study of MABp1, a first-in-human, first-true human monoclonal antibody against the II-1 in patients with advanced cancer," Molecular Cancer Therapeutics, 2011, (1 page).
Kumar, Suresh, et al: "Interleukin-1alpha promotes tumor growth and cachexia in MCF-7 xenograft model of breast cancer," American Journal of Pathology, 2003, vol. 163:2531-2541.
Ma, Joseph D et al: "Novel investigational biologies for the treatment of cancer cachexia," Expert Opin. Biol. Ther., 2014, vol. 14(8):1113-1120.
Madeddu, Clelia and Mantovani, Giovanni: "An update on promising agents for the treatment of cancer cachexia," Current Opinion in Supportive and Palliative Care, 2009, vol. 3:258-262.
Simard, John: "Early Results from XBiotech's Clinical Study in Cachexia Hint at Breakthrough Treatment," XBiotech News: Clinical Study in Cachex . . . , 2011, (3 pages), (retrieved from the Internet <http://www.xbiotech.com/about/news/early-results-from-xBiotechs-clinical-study-in-cachexia.html>, last visited on Jul. 22, 2015.
Tamura, Sumie et al: "Involvement of human interleukin 6 in experimental cachexia induced by a human uterine cervical carcinoma xenograft," Clinical Cancer Research, Nov. 1995, vol. 1:1353-1358.
Sturlan, Sanda, et al: "In vivo gene transfer of murine interleukin-4 inhibits colon-26-mediated cancer cachexia in mice," Anticancer Research, 2002, vol. 22:2547-2554.
Costelli, Paola et al: "Interleukin-1 receptor antagonist (IL-1ra) is unable to reverse cachexia in rats bearing an ascites hepatoma (Yoshida AH-130)," Cancer Letters 95, 1995, pp. 33-38.
Larsen C.M. et al. Interleukin-1-receptor antagonist is type 2 diabetes mellitus. New England Journal of Medicine, 2007, vol. 356, p. 1517-1526.
Larsen, C.M., et al. Sustained effects of interleukin-1 receptor antagonist treatment in type 2 diabetes. Diabetes Care, 2009, vol. 32, p. 1663-1668.
Levetan, C. Oral antidiabetic agents in type 2 diabetes. Current Medical Research and Opinion, 2007, vol. 23, No. 4, p. 945-952.
Van Asseldonk, E.J.P., et al. One week treatment with the IL-1 receptor antagonist anakinra leads to a sustained improvement in

(56) References Cited

OTHER PUBLICATIONS insulin sensitivity in insulin resistant patients with type 1 diabetes mellitus. Clinical Immunology, 2015, vol. 160, p. 155-162.
Tzanetakou, V. et al., "Safety and Efficacy of Anakinra in Severe Hidradenitis Suppurativa: A Randomized Clinical Trial", Jama Dermatology, (Jan. 2016), vol. 152, No. 1, doi:10.1001/jamadermatol. 2015.3903, ISSN 2168-6068, pp. 52-59, XP055617164.
Kanni, T. et al., "MABp1 Targeting IL-1a for Moderate to Severe Hidradenitis Suppurativa Not Eligible for Adalimumab: A Randomized Study", Journal of Investigative Dermatology, (Nov. 10, 2017), vol. 138, No. 4, ISSN 1523-1747, pp. 795-801, XP055532244.
GenBank, (May 19, 2005), Database accession No. AY510107.1, XP008146519.
Francois Mach., "Toward New Therapeutic Strategies Against Neointimal Formation in Restenosis", Arterioscler Thromb Vasc Biol, (2000), vol. 20, pp. 1699-1700, XP055244035.
Haller, M. "Converting Intravenous Dosing to Subcutaneous Dosing with Recombinant Human Hyaluronidase", Pharmaceutical Technology, Oct. 2, 2007, vol. 31, Issue 10 (Year: 2007).
Morton, A.C., et al., "Investigation of IL-1 Inhibition in Patients Presenting with Non-St Elevation Myocardial Infarction Acute Coronary Syndromes (The MRC ILA Heart Study), "Heart, vol. 97, Suppl 1., Jun. 2011, p. A13.
Schmidt, R. "Dose-Finding Studies in Clinical Drug Development"; EurJ Clin Pharmacol (1988) 34:15-19. (Year: 1988).
Walpole et al. "The weight of nations: an estimation of adult human biomass"; BMC Public Health 2012, 12:439. (Year: 2012) 6 pages.
Eisenhauer et al., Eur J Cancer. Jan. 2009;45(2):228-47.
Apte, Ron N. et al.: "The involvement of IL-1 in tumorigenesis, tumor invasiveness, metastasis and tumor-host interactions," Cancer Metastasis Rev, 2006, vol. 25:387-408.
Chang, Cheng-Hsien et al.: "Interleukin-1 alpha Released from Epithelial Cells after Adenovirus Type 37 Infection Activates Intercellular Adhesion Molecule 1 Expression on Human Vascular Endothelial Cells," Journal of Virology, 2002:427-431.
Lewis, Anne M. et al.: "Interleukin-I and cancer progression: the emerging role of interleukin-I receptor antagonist as a novel therapeutic agent in cancer treatment," Journal of Translational Medicine, 2006, vol. 4:1-12.
Lundberg, Ingrid et al.: "Cytokine production in muscle tissue of patients with idiopathic inflammatory myopathies," Arthritis & Rheumatism, 1997, vol. 40, No. 5:865-874.
Orjalo, Arturo V. et al.: "Cell surface-bound IL-1alpha is an upstream regulator of the senescence-associated IL-6/IL-8 cytokine network," PNAS, 2009, vol. 106, No. 40:17031-17036.
Pazzaglia, Laura et al.: "Activation of metalloproteinases-2 and -9 by Interleukin-1 alpha in S100A4-positive Liposarcoma Cell Line: Correlation with Cell Invasiveness," Anticancer Research, 2004, vol. 24:967-972.
Tsunoda, Yasuaki, "Immunohistochemical Study of Cytokines and Extracellular Matrices at Invasive Sites of Human Colon Cancers," Biotherapy, 1996, vol. 10 (No. 5):789-790.
Lapins et al., "Coagulase-negative staphylococci are the most common bacteria found in cultures from the deep portions of hidradenitis suppurativa lesions, as obtained by carbon dioxide laser surgery". British Journal of Dermatology. 1999; 140: 90-95.
Schultz, et al., "Endogenous interleukin-1a promotes a proliferative and proinflammatory phenotype in human vascular smooth muscle cells," Am J Physiol Heart Circ Physiol, Jun. 2007; 292(6): H2927-34.
NCT01270945—Safety and Preliminary Efficacy Study of an Anti inflammatory Therapeutic Antibody in Reducing Restenosis (version 6; submitted May 15, 2012). (8 pages).
Wei et al., "Clinical key techniques of routine operation in cardiac diagnosis and treatment", Science and Technology Literature Press, 1st edition—"Restenosis and related factors", p. 239, publication date: May 2009. Chinese-language publication. English translation of relevant excerpt attached. (1 page).
Peigang et al., "Theory and Practice of Neurosurgical Diseases", Tianjin Science and Technology Press, 1st edition—Complications and Countermeasures of Stent Implantation, p. 123, publication date: Oct. 2011. Chinese-language publication. English translation of relevant excerpt attached. (1 page).
Sun Qinguo et al., "Coronary Heart Disease", chiefly edited by China Medical Science and Technology Press, 1st edition, "Interventional Therapy of Coronary Heart Disease", pp. 203-208, publication date: Jan. 2010. Chinese-language publication. English translation of relevant excerpt attached. (1 page).
Chamberlain, Janet et al., "Interleukin-1B and signaling of Interleukin-1 in Vascular Wall and Circulating Cells Modulates the Extend of Neointima Formation in Mice," American Journal of Pathology, vol. 168, No. 4, pp. 1396-1403, Apr. 2006.
Morton, Allison C., et al., "The effect of interleukin-1 receptor antagonist therapy on markers of inflammation in non-ST elevation acute coronary syndromes: the MRC-ILA Heart Study," European Heart Journal, vol. 36, pp. 377-384 (2015).
Clinical trial: NCT02643654, "MABp1 in Hidradenitis Suppurativa Refractory to Adalimumab", Oct. 9, 2016 (Oct. 9, 2016), Retrieved from the Internet: URL: https://https://clinicaltrials.gov/ct2/show/NCT02643654. (10 pages).
Hessam, et al., "Microbial Profile and Antimicrobial Susceptibility of Bacteria Found in Inflammatory Hidradenitis Suppurativa Lesions," Skin Pharmacol Physiol 2016; 29:161-167.
Rishi et al., "Hospital anxiety and depression scale assessment of 100 patients before and after using low vision care: A prospective study in a teriary eye-care setting," Indian J Ophthalmol. Nov. 2017; 65(11): 1203-1208.
Westhuis et al., "Develepment and Validation of the Clinical Anxiety Scale: A Rapid Assessment Instrument for Empirical Practice," Educational and Psychological Measurement, 49:153-163, 1989.
Snaith, R.P. The Hospital Anxiety and Depression Scale. Health Qual Life Outcomes 1, 29 (2003). (4 pages).
Ramli et al., "Acne analysis, grading and computational assessment methods: an overview," Skin Research and Technology 2012; 18: 1-14.
Mennin et al., "Screening for social anxiety disorder in the clinical settin: using the Liebowitz Social Anxiety Scale," Anxiety Disorders, 16:661-673, 2002.
US National Institutes of Health, "Anakinra With or Without Dexamethasone in Treating Patients With Smoldering or Indolent Multiple Myeloma", ClinicalTrials.gov, US, (Mar. 12, 2008), pp. 1-4, ClinicalTrials.gov, URL: http://clinicaltrials.gov/ct2/show/NCT00635154.
Janik et al., "Phase II trial of interleukin 1 alpha and indomethacin in treatment of metastatic melanoma.", Journal of the National Cancer Institute Jan. 3, 1996 (Jan. 3, 1996), vol. 88, No. 1, pp. 44-49; https://doi.org/10.1093/jnci/88.1.44.
Radke et al., "Outcome after treatment of coronary in-stent restenosis results from a systematic review using meta-analysis techniques", European Heart Journal, vol. 24, No. 3, Feb. 1, 2003 (Feb. 1, 2003), pp. 266-273, XP055265672, GB ISSN: 0195-668X, DOI: 10.1016/S0195-668X(02)00202-6.
Ofran et al., "Automated Identification of Complementarity Determining Regions (CDRs) Peculiar Characteristics of CDRs and B Cell Epitopes", J. Immunology 2008 181: 6230-6235.
Lewis et al., "Interleukin-I and cancer progression: the emerging role of interleukin-I receptor antagonist as a novel therapeutic agent in cancer treatment," Journal of Translational Medicine, Nov. 10, 2006, 4:48.
Huey-Huey Chua et al., "Regulation of IAPs Gene Family by Interleukin-1α and Epstein-Barr Virus in Nasopharyngeal Carcinoma," Head & Neck 30, No. 12 (2008): 1575-85.
Yoichi Matsuo et al., "IL-1α Secreted by Colon Cancer Cells Enhances Angiogenesis: The Relationship between IL-1α Release and Tumor Cells' Potential for Liver Metastasis," Journal of Surgical Oncology 99, No. 6 (2009): 361-67.
Ron N. Apte et al., "The Involvement of IL-1 in Tumorigenesis, Tumor Invasiveness, Metastasis and Tumor-Host Interactions," Cancer and Metastasis Reviews 25, No. 3 (Sep. 1, 2006): 387-408.
Tumor Metastasis, chiefly-edited by Liao Zijun, p. 59, Shaanxi Science & Technology Press, Feb. 28, 2007.

(56) References Cited

OTHER PUBLICATIONS

Johnson el al., "Relationships between drug activity in NCI preclinical in vitro and in vivo models and early clinical trials," British Journal of Cancer, vol. 84 (10), pp. 1424-1431, (2001).
Morrison, Sherie L., et al., "Chimeric human antibody molecules: Mouse antigen-binding domains with human constant region domains," Proc. Natl. Acad. Sci. USA, vol. 81, pp. 6851-6855, Nov. 1984.
Neuberger, Michael S., et al., "Rcombinant antibodies possessing novel effector functions," Nature, vol. 312, pp. 604-608 (1984) (Abstract Only).
Takeda, Shun-ichi, et al., "Construction of chimaeric processed immunoglobulin genes containing mouse variable and human constant region sequences," Nature, vol. 314, pp. 452-454 (1985) (Abstract Only).
Marks, James D., et al., "By-Passing Immunization: Building High Affinity Human Antibodies by Chain Shuffling," Bio/Technology, vol. 10, pp. 779-783 (1992) (Abstract Only).
Barbas, C.F., et al., "In vitro evolution of a neutralizing human antibody to human immunodeficiency virus type 1 to enhance affinity and broaden strain cross-reactivity," Proc. Natl. Acad. Scie. USA, vol. 91, pp. 3809-3813, Apr. 1994.
Schier, Robert, et al., "Identification of functional and structural amino-acid residues by parsimonious mutagenesis," Gene, vol. 169, Issue 2, pp. 147-155 (1996) (Abstract Only).
Yelton, D.E., et al., "Affinity maturation of the BR96 anti-carcinoma antibody by codon-based mutagenesis," J. Immunology, vol. 155, No. 4, pp. 1994-2004, Aug. 15, 1995 (Abstract Only).
Jackson, J.R., et al., "In vitro antibody maturation. Improvement of a high affinity, neutralizing antibody against IL-1 beta," J. Immunology, vol. 154, No. 7, pp. 3310-3319, Apr. 1, 1995 (Abstract Only).
Hawkins, Robert E., et al., "Selection of phage antibodies by binding affinity: Mimicking affinity maturation," J. Mol. Biol., vol. 226, Issue 3, pp. 889-896, Aug. 5, 1992 (Abstract Only).
Kam, Nadine Wong Shi, et al., "Carbon nanotubes as multifinctional biological transporters and near-infrared agents for selective cancer cell destruction," Proc. Natl. Acad. Sci, USA, vol. 102, No. 33, pp. 11600-11605, Aug. 16, 2005.
Draber, Pavel, et al., "Stability of monoclonal IgM antibodies freeze-dried in the presence of trehalose," J. Immunol. Methods, vol. 181, Issue 1, pp. 37-43, Apr. 12, 1995 (Abstract Only).
Gillet, Jean-Pierre, et al., "Redefining the relevance of established cancer cell lines to the study of mechanisms of clinical anti-cancer drug resistance," PNAS, vol. 108, No. 46, pp. 18708-18713, Nov. 15, 2011.
Elaraj, Dina M., et al., "The Role of Interleukin 1 in Growth and Metastasis of Human Cancer Xenografts," Clin. Cancer Res., vol. 12, No. 4, pp. 1088-1096, Feb. 15, 2006.
Busson, Pierre, et al., "Espstein-Barr virus-containing epithelial cells from nasopharyngeal carcinoma produce interleuikin 1a," Proc. Natl. Acad. Sci, USA, vol. 84, pp. 6262-6266, Sep. 1987.
Lundberg, Ingrid, et al., "Decreased expression of interleukin-1a, interleukin-1b, and cell adhesion molecules in muscle tissue following corticosteroid treatment in patients with polymyositis and dermatomyositis," Arthritis & Rheumatology, vol. 43, No. 2, Feb. 2000, see https://doi.org/10.1002/1529-0131(200002)43:2%3C336::AID-ANR13%3E3.0.CO;2-V.
Goding, James W., Monoclonal Antibodies, Principles and Practice, Academic Press, London, Second Edition, 1996.
Sondermann, Wiebke, et al., "Exacerbated Psoriasis as a Rare Trigger of Multilocular Pyoderma Gangrenosum: A Case Report of a Rare Coincidence," Internationl Journal of Lower Extremity Wounds, 00(0), pp. 1-3 (2022).
Hao Guo, "Pyoderma gangrenosum associated with ulcerative colitis and psoriasis," Chin Med J. vol. 126, No. 9 (2013).
McKenzie, Fatima, "Biologic and small-molecule medications in the management of pyoderma gangrenosum," Journal of Dermatological Treatment, vol. 30, No. 3, pp. 264-276 (2019).
Lim, Shi Yu Derek, et al., "Systematic review of immunomodulatory therapies for hidradenitis suppurativa," Biologics: Targets and Therapy, vol. 13, pp. 53-78 (2019).
International Search Report dated Jul. 16, 2021 in PCT/US2021/027614.
Burgdorf, Birte, et al., "Successful treatment of a refractory pyoderma gangrenosum with risankizumab," Int. Wound J. vol 17, pp. 1086-1088 (2020).
Maronese, Carlo Alberto, et al., "Pyoderma Gangrenosum: An Updated Literature Review on Established and Emerging Pharmacological Treatments," American Journal of Clinal Dermatology, Published online: May 24, 2022 see https://doi.org/10.1007/s40257-022-00699-8.
NCT01965613, Jan. 2021.
Ambiru, et al., "Type IV collagenase activities in human colorectal cancers and its role in cancer invasion and metastasis," Journal of the Japanese Society of Gastroenterology, vol. 90, No. 7, pp. 1555-1561 (1993).
Okada, Tomoko, et al., "role of endothelial Cells in tumor Metastasis," Japanese Journal of thrombosis and Hemostasis, vol. 3, No. 1, pp. 12-21 (1992).
Rhodus, Nelson L., et al., "A comparison of the pro-inflammatory, NF-kB-dependent cytokines: TNF-alpha, IL-1-alpha, IL-6, and IL-8 in different oral fluids from oral lichen planus patients," Clinical Immunology, vol. 114, pp. 278-283 (2005).
Wen Zhaoming, "Diagnosis and Treatment of Allergic Diseases: From Infants to Adults," China Medical Science and Technology Press, pp. 252, Oct. 1997. An English translation of the relevant excerpt from this document is attached).

\* cited by examiner

TREATMENT FOR NEOPLASTIC DISEASES

CROSS-REFERENCE TO RELATED APPLICATIONS

The present application is a continuation application of U.S. nonprovisional patent application Ser. No. 13/215,464 filed on Aug. 23, 2011, which claims the priority of U.S. provisional patent application Ser. Nos. 61/376,097 filed on Aug. 23, 2010, 61/406,759 filed on Oct. 26, 2010, 61/411,183 filed on Nov. 8, 2010, and 61/480,635 filed on Apr. 29, 2011, all of which are incorporated herein by reference in their entirety.

STATEMENT AS TO FEDERALLY SPONSORED RESEARCH

Not applicable.

FIELD OF THE INVENTION

The invention relates generally to the fields of medicine, oncology, and immunology. More particularly, the invention relates to the use of antibodies (Abs) which specifically bind interleukin-1α (IL-1α) to treat a tumor-associated disease and other tumor-associated pathologies.

BACKGROUND

Despite many advances, tumor-associated diseases such as cancer remain one of the leading causes of death and morbidity in developed nations. Although many of the molecular mechanisms of tumorigenesis have now been revealed, standard treatment of most aggressive tumors continues to be surgical resection, chemotherapy, and radiotherapy. While increasingly successful, each of these treatments still causes numerous undesired side effects. For example, surgery results in pain, traumatic injury to healthy tissue, and scarring. Radiotherapy and chemotherapy cause nausea, immune suppression, gastric ulceration, and secondary tumorigenesis.

Over the last several years much progress has been made using biologic agents such as Abs to treat cancerous tumors. Abs can directly target specific types of tumor cells to harness a patient's immune response to kill the tumor. Alternatively, they can target cell growth factors to interfere with the growth of tumor cells. As with conventional chemotherapeutic agents, not all anti-tumor Abs are useful for treating all types of neoplasms, and many initially effective antibodies later lose potency. Thus new anti-tumor Abs are needed.

SUMMARY

The invention is based on the discovery that a mAb that specifically binds IL-1α is useful for treating various tumor-associated diseases.

Accordingly, the invention features a medicament and method for treating neoplastic diseases (e.g., a colorectal cancer such as one having a KRAS mutation, an EBV-associated cancer such as nasopharygeal carcinoma or Burkitt's lymphoma, non-small cell lung cancer (NSCLC) or non-cancerous conditions associated with tumors such as Castleman's disease) in a human subject. The method can be performed by administering to the subject a pharmaceutical composition including a pharmaceutically acceptable carrier and an amount of an anti-IL-1α Ab effective to ameliorate a symptom of a tumor-associated pathology and/or to reduce the size of a tumor in the subject by at least about 10% (e.g., at least 8, 9, 10, 15, 17, 20, 30, 40, 50, 60, 70, 80, 90, or 100%). The medicament can include an anti-IL-1α Ab. The anti-IL-1α Ab can be a mAb such as an IgG1. The anti-IL-1α Ab can be the mAb designated as MABp1 or a mAb that includes one or more complementarity determining regions (CDRs) of MABp1.

The pharmaceutical composition can be administered to the subject by injection, subcutaneously, intravenously, intramuscularly, or directly into a tumor. In the method, the dose can be at least 0.25 (e.g., at least 0.2, 0.5, 0.75, 1, 2, 3, 4, or 5) mg/ml.

Unless otherwise defined, all technical terms used herein have the same meaning as commonly understood by one of ordinary skill in the art to which this invention belongs. Commonly understood definitions of biological terms can be found in Rieger et al., Glossary of Genetics: Classical and Molecular, 5th edition, Springer-Verlag: New York, 1991; and Lewin, Genes V, Oxford University Press: New York, 1994. Commonly understood definitions of medical terms can be found in Stedman's Medical Dictionary, 27th Edition, Lippincott, Williams & Wilkins, 2000.

As used herein, an "Ab" or "Ab" is an immunoglobulin (Ig), a solution of identical or heterogeneous Igs, or a mixture of Igs. An "Ab" can also refer to fragments and engineered versions of Igs such as Fab, Fab', and F(ab')$_2$ fragments; and scFv's, heteroconjugate Abs, and similar artificial molecules that employ Ig-derived CDRs to impart antigen specificity. A "mAb" or "mAb" is an Ab expressed by one clonal B cell line or a population of Ab molecules that contains only one species of an antigen binding site capable of immunoreacting with a particular epitope of a particular antigen. A "polyclonal Ab" or "polyclonal Ab" is a mixture of heterogeneous Abs. Typically, a polyclonal Ab will include myriad different Ab molecules which bind a particular antigen with at least some of the different Abs immunoreacting with a different epitope of the antigen. As used herein, a polyclonal Ab can be a mixture of two or more mAbs.

An "antigen-binding portion" of an Ab is contained within the variable region of the Fab portion of an Ab and is the portion of the Ab that confers antigen specificity to the Ab (i.e., typically the three-dimensional pocket formed by the CDRs of the heavy and light chains of the Ab). A "Fab portion" or "Fab region" is the proteolytic fragment of a papain-digested Ig that contains the antigen-binding portion of that Ig. A "non-Fab portion" is that portion of an Ab not within the Fab portion, e.g., an "Fc portion" or "Fc region." A "constant region" of an Ab is that portion of the Ab outside of the variable region. Generally encompassed within the constant region is the "effector portion" of an Ab, which is the portion of an Ab that is responsible for binding other immune system components that facilitate the immune response. Thus, for example, the site on an Ab that binds complement components or Fc receptors (not via its antigen-binding portion) is an effector portion of that Ab.

When referring to a protein molecule such as an Ab, "purified" means separated from components that naturally accompany such molecules. Typically, an Ab or protein is purified when it is at least about 10% (e.g., 9%, 10%, 20%, 30% 40%, 50%, 60%, 70%, 80%, 90%, 95%, 98%, 99%, 99.9%, and 100%), by weight, free from the non-Ab proteins or other naturally-occurring organic molecules with which it is naturally associated. Purity can be measured by any appropriate method, e.g., column chromatography, polyacrylamide gel electrophoresis, or HPLC analysis. A chemically-synthesized protein or other recombinant protein produced in a cell type other than the cell type in which it naturally occurs is "purified."

By "bind", "binds", or "reacts with" is meant that one molecule recognizes and adheres to a particular second molecule in a sample, but does not substantially recognize or adhere to other molecules in the sample. Generally, an Ab that "specifically binds" another molecule has a $K_d$ greater than about $10^5$, $10^6$, $10^7$, $10^8$, $10^9$, $10^{10}$, $10^{11}$, or $10^{12}$ liters/mole for that other molecule.

A "therapeutically effective amount" is an amount which is capable of producing a medically desirable effect in a treated animal or human (e.g., amelioration or prevention of a disease or symptom of a disease).

Although methods and materials similar or equivalent to those described herein can be used in the practice or testing of the present invention, suitable methods and materials are described below. All publications mentioned herein are incorporated by reference in their entirety. In the case of conflict, the present specification, including definitions will control. In addition, the particular embodiments discussed below are illustrative only and not intended to be limiting.

DETAILED DESCRIPTION

The invention encompasses compositions and methods for ameliorating one or more symptoms of a tumor-associated pathology in a subject. The below described preferred embodiments illustrate adaptation of these compositions and methods. Nonetheless, from the description of these embodiments, other aspects of the invention can be made and/or practiced based on the description provided below.

General Methodology

Methods involving conventional immunological and molecular biological techniques are described herein Immunological methods (for example, assays for detection and localization of antigen-Ab complexes, immunoprecipitation, immunoblotting, and the like) are generally known in the art and described in methodology treatises such as Current Protocols in Immunology, Coligan et al., ed., John Wiley & Sons, New York. Techniques of molecular biology are described in detail in treatises such as Molecular Cloning: A Laboratory Manual, 2nd ed., vol. 1-3, Sambrook et al., ed., Cold Spring Harbor Laboratory Press, Cold Spring Harbor, N.Y., 2001; and Current Protocols in Molecular Biology, Ausubel et al., ed., Greene Publishing and Wiley-Interscience, New York. Ab methods are described in Handbook of Therapeutic Abs, Dubel, S., ed., Wiley-VCH, 2007. General methods of medical treatment are described in McPhee and Papadakis, Current Medical Diagnosis and Treatment 2010, 49$^{th}$ Edition, McGraw-Hill Medical, 2010; and Fauci et al., Harrison's Principles of Internal Medicine, 17$^{th}$ Edition, McGraw-Hill Professional, 2008

Treatment of a Tumor-Associated Disease

The compositions and methods described herein are useful for treating a tumor-associated disease in a mammalian subject by administering to the subject a pharmaceutical composition including an amount of an anti-IL-1α Ab effective to improve at least one characteristic of the tumor-associated disease in the subject. The mammalian subject might be any that suffers from a tumor-associated disease including, human beings, dogs, cats, horses, cattle, sheep, goats, and pigs. Human subjects might be male, female, adults, children, seniors (65 and older), and those with other diseases. Particularly preferred subjects are those whose disease has progressed after treatment with chemotherapy, radiotherapy, surgery, and/or biologic agents. Any type of a tumor-associated disease susceptible to treatment with an anti-IL-1α Ab might be targeted. Anti-IL-1α Ab administration is thought to be particularly effective for treating colorectal tumors (e.g., colorectal cancers with a KRAS mutation), EBV-associated neoplasms such as nasopharyngeal cancer or Burkitt's lymphoma, NSCLC, and blood cell neoplasms such as in Castleman's disease. A disease with tumors expressing IL-1α or tumors infiltrated with IL-1α inflammatory cells might also be targeted. The particular characteristic of a tumor-associated disease to be improved can be tumor size (e.g., T0, Tis, or T1-4), state of metastasis (e.g., M0, M1), number of observable tumors, node involvement (e.g., N0, N1-4, Nx), grade (i.e., grades 1, 2, 3, or 4), stage (e.g., 0, I, II, III, or IV), presence or concentration of certain markers on the cells or in bodily fluids (e.g., AFP, B2M, beta-HCG, BTA, CA 15-3, CA 27.29, CA 125, CA 72.4, CA 19-9, calcitonin, CEA, chromgrainin A, EGFR, hormone receptors, HER2, HCG, immunoglobulins, NSE, NMP22, PSA, PAP, PSMA, S-100, TA-90, and thyroglobulin), and/or associated pathologies (e.g., ascites or edema) or symptoms (e.g., cachexia, fever, anorexia, or pain). The improvement, if measurable by percent, can be at least 5, 10, 15, 20, 25, 30, 40, 50, 60, 70, 80, or 90% (e.g., volume or linear dimensions of a tumor).

Antibodies and Other Agents that Target IL-1α

Any suitable type of Ab or other biologic agent (e.g., a fusion protein including an IL-1α-binding component such as an IL-1 receptor) that specifically binds IL-1α and reduces a characteristic of a tumor-associated disease in a subject might be used in the invention. For example, the anti-IL-1α Ab used might be mAb, a polyclonal Ab, a mixture of mAbs, or an Ab fragment or engineered Ab-like molecule such as an scFv. The Ka of the Ab is preferably at least $1\times10^9$ M$^{-1}$ or greater (e.g., greater than $9\times10^{10}$ M$^{-1}$, $8\times10^{10}$ M$^{-1}$, $7\times10^{10}$ M$^{-1}$, $6\times10^{10}$ M$^{-1}$, $5\times10^{10}$ M$^{-1}$, $4\times10^{10}$ M$^{-1}$, $3\times10^{10}$ M$^{-1}$, $2\times10^{10}$ M$^{-1}$, or $1\times10^{10}$ M$^{-1}$). In a preferred embodiment, the invention utilizes a fully human mAb that includes (i) an antigen-binding variable region that exhibits very high binding affinity (e.g., at least nano or picomolar) for human IL-1α and (ii) a constant region. The human Ab is preferably an IgG1, although it might be of a different isotype such as IgM, IgA, or IgE, or subclass such as IgG2, IgG3, or IgG4. One example of a particularly useful mAb is MABp1, an IL-1α-specific IgG1 mAb described in U.S. patent application Ser. No. 12/455,458 filed on Jun. 1, 2009. Other useful mAbs are those that include at least one but preferably all the CDRs of MABp1.

Because B lymphocytes which express Ig specific for human IL-1α occur naturally in human beings, a presently preferred method for raising mAbs is to first isolate such a B lymphocyte from a subject and then immortalize it so that it can be continuously replicated in culture. Subjects lacking large numbers of naturally occurring B lymphocytes which express Ig specific for human IL-1α may be immunized with one or more human IL-1α antigens to increase the number of such B lymphocytes. Human mAbs are prepared by immortalizing a human Ab secreting cell (e.g., a human plasma cell). See, e.g., U.S. Pat. No. 4,634,664.

In an exemplary method, one or more (e.g., 5, 10, 25, 50, 100, 1000, or more) human subjects are screened for the presence of such human IL-1α-specific Ab in their blood.

Those subjects that express the desired Ab can then be used as B lymphocyte donors. In one possible method, peripheral blood is obtained from a human donor that possesses B lymphocytes that express human IL-1α-specific Ab. Such B lymphocytes are then isolated from the blood sample, e.g., by cells sorting (e.g., fluorescence activated cell sorting, "FACS"; or magnetic bead cell sorting) to select B lymphocytes expressing human IL-1α-specific Ig. These cells can then be immortalized by viral transformation (e.g., using EBV) or by fusion to another immortalized cell such as a human myeloma according to known techniques. The B lymphocytes within this population that express Ig specific for human IL-1α can then be isolated by limiting dilution methods (e.g., cells in wells of a microtiter plate that are positive for Ig specific for human IL-1α are selected and subcultured, and the process repeated until a desired clonal line can be isolated). See, e.g., Goding, MAbs: Principles and Practice, pp. 59-103, Academic Press, 1986. Those clonal cell lines that express Ig having at least nanomolar or picomolar binding affinities for human IL-1α are preferred. MAbs secreted by these clonal cell lines can be purified from the culture medium or a bodily fluid (e.g., ascites) by conventional Ig purification procedures such as salt cuts, size exclusion, ion exchange separation, and affinity chromatography.

Although immortalized B lymphocytes might be used in in vitro cultures to directly produce mAbs, in certain cases it might be desirable to use heterologous expression systems to produce mAbs. See, e.g., the methods described in U.S. patent application Ser. No. 11/754,899. For example, the genes encoding an mAb specific for human IL-1α might be cloned and introduced into an expression vector (e.g., a plasmid-based expression vector) for expression in a heterologous host cell (e.g., CHO cells, COS cells, myeloma cells, and *E. coli* cells). Because Igs include heavy (H) and light (L) chains in an $H_2L_2$ configuration, the genes encoding each may be separately isolated and expressed in different vectors.

Although generally less preferred due to the greater likelihood that a subject will develop an anti-Ab response, chimeric mAbs (e.g., "humanized" mAbs), which are antigen-binding molecules having different portions derived from different animal species (e.g., variable region of a mouse Ig fused to the constant region of a human Ig), might be used in the invention. Such chimeric Abs can be prepared by methods known in the art. See, e.g., Morrison et al., Proc. Nat'l. Acad. Sci. USA, 81:6851, 1984; Neuberger et al., Nature, 312:604, 1984; Takeda et al., Nature, 314:452, 1984. Similarly, Abs can be humanized by methods known in the art. For example, mAbs with a desired binding specificity can be humanized by various vendors or as described in U.S. Pat. Nos. 5,693,762; 5,530,101; or 5,585,089.

The mAbs described herein might be affinity matured to enhance or otherwise alter their binding specificity by known methods such as VH and VL domain shuffling (Marks et al. Bio/Technology 10:779-783, 1992), random mutagenesis of the hypervariable regions (HVRs) and/or framework residues (Barbas et al. Proc Nat. Acad. Sci. USA 91:3809-3813, 1994; Schier et al. Gene 169:147-155, 1995; Yelton et al. J. Immunol. 155:1994-2004, 1995; Jackson et al., J. Immunol. 154(7):3310-9, 1995; and Hawkins et al, J. Mol. Biol. 226:889-896, 1992. Amino acid sequence variants of an Ab may be prepared by introducing appropriate changes into the nucleotide sequence encoding the Ab. In addition, modifications to nucleic acid sequences encoding mAbs might be altered (e.g., without changing the amino acid sequence of the mAb) for enhancing production of the mAb in certain expression systems (e.g., intron elimination and/or codon optimization for a given expression system). The mAbs described herein can also be modified by conjugation to another protein (e.g., another mAb) or non-protein molecule. For example, a mAb might be conjugated to a water soluble polymer such as polyethylene glycol or a carbon nanotube (See, e.g., Kam et al., Proc. Natl. Acad. Sci. USA 102: 11600-11605, 2005). See, U.S. patent application Ser. No. 11/754,899.

Preferably, to ensure that high titers of human IL-1α-specific mAb can be administered to a subject with minimal adverse effects, the mAb compositions of the invention are at least 0.5, 1, 2, 3, 4, 5, 6, 7, 8, 9, 10, 11, 12, 13, 14, 15, 20, 25, 30, 35, 40, 45, 50, 60, 70, 80, 90, 95, 96, 97, 98, 99, 99.9 or more percent by weight pure (excluding any excipients). The mAb compositions of the invention might include only a single type of mAb (i.e., one produced from a single clonal B lymphocyte line) or might include a mixture of two or more (e.g., 2, 3, 4, 5, 6, 7, 8, 9, 10 or more) different types of mAbs.

To modify or enhance their function, the human IL-1α mAbs might be conjugated with another molecule such as a cytotoxin. A human IL-1α specific mAb might be conjugated with one or more cytotoxins to more effectively kill cells expressing IL-1α. Cytotoxins for use in the invention can be any cytotoxic agent (e.g., molecule that can kill a cell after contacting the cell) that can be conjugated to a human IL-1α specific mAb. Examples of cytotoxins include, without limitation, radionuclides (e.g., $^{35}S$, $^{14}C$, $^{32}P$, $^{125}I$, $^{131}I$, $^{90}Y$, $^{89}Zr$, $^{201}Tl$, $^{186}Re$, $^{188}Re$, $^{57}Cu$, $^{213}Bi$, and $^{211}At$), conjugated radionuclides, and chemotherapeutic agents. Further examples of cytotoxins include, but are not limited to, antimetabolites (e.g., 5-fluorouricil (5-FU), methotrexate (MTX), fludarabine, etc.), anti-microtubule agents (e.g., vincristine, vinblastine, colchicine, taxanes (such as paclitaxel and docetaxel), etc.), alkylating agents (e.g., cyclophasphamide, melphalan, bischloroethylnitrosurea (BCNU), etc.), platinum agents (e.g., cisplatin (also termed cDDP), carboplatin, oxaliplatin, JM-216, CI-973, etc.), anthracyclines (e.g., doxorubicin, daunorubicin, etc.), antibiotic agents (e.g., mitomycin-C), topoisomerase inhibitors (e.g., etoposide, tenoposide, and camptothecins), or other cytotoxic agents such as ricin, diptheria toxin (DT), *Pseudomonas* exotoxin (PE) A, PE40, abrin, saporin, pokeweed viral protein, ethidium bromide, glucocorticoid, anthrax toxin and others. See, e.g., U.S. Pat. No. 5,932,188.

While the IL-1α specific Abs described above are preferred for use in the invention, in some cases, other agents that specifically target IL-1α might be used so long as their administration leads to improvement of a characteristic of a tumor-associated disease. These other agents might include small organic molecules, aptamers, peptides, and proteins that specifically bind IL-1α (e.g., anakinra or rilonacept).

Pharmaceutical Compositions and Methods

The anti-IL-1α Ab compositions may be administered to animals or humans in pharmaceutically acceptable carriers (e.g., sterile saline), that are selected on the basis of mode and route of administration and standard pharmaceutical practice. A list of pharmaceutically acceptable carriers, as well as pharmaceutical formulations, can be found in Remington's Pharmaceutical Sciences, a standard text in this field, and in USP/NF. Other substances may be added to the compositions and other steps taken to stabilize and/or preserve the compositions, and/or to facilitate their administration to a subject.

For example, the Ab compositions might be lyophilized (see Draber et al., J. Immunol. Methods. 181:37, 1995; and PCT/US90/01383); dissolved in a solution including sodium and chloride ions; dissolved in a solution including one or more stabilizing agents such as albumin, glucose, maltose, sucrose, sorbitol, polyethylene glycol, and glycine; filtered (e.g., using a 0.45 and/or 0.2 micron filter); contacted with beta-propiolactone; and/or dissolved in a solution including a microbicide (e.g., a detergent, an organic solvent, and a mixture of a detergent and organic solvent.

The Ab compositions may be administered to animals or humans by any suitable technique. Typically, such administration will be parenteral (e.g., intravenous, subcutaneous, intramuscular, or intraperitoneal introduction). The compositions may also be administered directly to the target site (e.g., intratumorally) by, for example, injection. Other methods of delivery, e.g., liposomal delivery or diffusion from a device impregnated with the composition, are known in the art. The composition may be administered in a single bolus, multiple injections, or by continuous infusion (e.g., intravenously or by peritoneal dialysis).

A therapeutically effective amount is an amount which is capable of producing a medically desirable result in a treated animal or human. An effective amount of anti-IL-1α Ab compositions is an amount which shows clinical efficacy in patients as measured by the improvement in one or more a tumor-associated disease characteristics described above. As is well known in the medical arts, dosage for any one animal or human depends on many factors, including the subject's size, body surface area, age, the particular composition to be administered, sex, time and route of administration, general health, and other drugs being administered concurrently. Preferred doses range from about 0.2 to 20 (e.g., 0.15, 0.2, 0.3, 0.4, 0.5, 1, 2, 3, 4, 5, 6, 7, 8, 9, 10, 15, 20, 30, 50, or 100) mg/kg body weight. The dose may be given repeatedly, e.g., hourly, daily, semi-weekly, weekly, bi-weekly, tri-weekly, or monthly.

Examples

Example 1—Xilonix™

Xilonix™ is a sterile injectable liquid formulation of 15 mg/mL MABp1 in a stabilizing isotonic buffer (pH 6.4). Each 10-mL Type I borosilicate glass serum vial contains 5 mL of the formulation, and is sealed with a 20-mm Daikyo Flurotec butyl rubber stopper and flip-off aluminum seal. The product is stored at 5±3° C., with excursions to room temperature permitted. The exact composition of the drug product is shown below:

| Composition of the Drug Product (Xilonix ™) | | | |
|---|---|---|---|
| Ingredient | Grade | Manufacturer | Concentration |
| MABp1 Ab | GMP | XBiotech | 15 mg/mL |
| sodium phosphate dibasic | compendial | J T Baker | 12 mg/mL |
| citric acid monohydrate | compendial | J T Baker | 2 mg/mL |
| Trehalose•2H2O (high-purity low endotoxin) | compendial | Ferro-Pfanstiehl | 60 mg/mL |
| polysorbate 80 | compendial | J T Baker | 0.2 mg/mL |
| Phosphoric acid, to adjust pH | compendial | J T Baker | 0.04 mg/mL |
| water for injection | compendial | Microbix | q.s. |

Method of Administration:

The calculated volume is withdrawn from the drug (mAb)-containing vial(s) using a suitable syringe. The drug is then injected into a small IV bag containing 100 mL of normal saline (0.9% NaCl) and mixed by inversion. The diluted drug product can be stored at room temperature for 3 hours prior to administration and is infused over a 1-hour period, with the subject being monitored for signs of an infusion reaction. The infusion is chased with a minimum of 30 mLs of normal saline to deliver any product that may be held up in the infusion set.

Example 2—Treatment of Colorectal Cancer with an IL-1α-Specific MAb (Xilonix™)

The human subject was a 63 year-old female diagnosed with metastatic colorectal cancer (KRAS mutation positive). Prior to treatment with Xilonix™, the subject underwent right hemicolectomy and was reportedly staged T3N1MX. She thereafter received adjuvant chemotherapy with FOLFOX for a total of 12 cycles over about six months. A PET CT scan performed about two months after completion of FOLFOX revealed a mass in her pelvis. The subject was hospitalized at the time for placement of ureteral stent due to obstructive hydronephrosis apparently from the tumor. She started FOLFIRI and Avastin shortly thereafter and received 8 cycles of therapy. The subject then underwent re-staging PET CT scan which confirmed disease in the pelvis, and also revealed small pulmonary nodules consistent with metastatic disease. A CT scan of the chest, abdomen and pelvis revealed a 12 cm pelvic mass, a 2 cm omental mass, and the hydronephrosis on the right side with associated ureteral stent. She received 2 extra cycles of FOLFIRI and Avastin. A subsequent PET CT scan showed progression of the bilateral pulmonary nodules. The subject then started irinotecan and Erbitux® (Cetuximab) therapy. A follow up PET CT scan demonstrated disease progression in the lungs.

The subject was initiated on a phase 1 trial with Doxil® (Doxorubicin Liposomal), Velcade® (Bortezomib), and Gemzar® (Gemcitabine) but unfortunately the first re-staging suggested disease progression. She also completed another phase 1 trial with oxaliplatin in combination with azacitydineon and completed 2 cycles before disease progression. At the conclusion of her participation on this last clinical phase 1 trial, the subject was enrolled in the current clinical trial.

She was enrolled in the first dosing cohort (0.25 mg/ml) and completed 5-21 day cycles on the protocol, thus receiving a total of five infusions of MABp1 (0.25 mg/kg) every 21 days. The subject's dose was increased to 0.75 mg/kg on Cycle 6 Day 1. An initial PET CT scan revealed about a 17% reduction in the sum of diameters in the patient's tumors that were being tracked. Following additional doses of MABp1, an over 30% reduction in the sum of diameters in the patient's tracked tumors was observed. A Chest CT showed a paratrocheal lymph node that previously measured 3.5 cm was reduced to 2.9 cm at the end of Cycle 6. A left lung metastasis decreased from 2.2 cm to 1.9 cm, and an implant from the left rectus muscle decreased from 3.2 cm to 2.7 cm. The CEA tumor marker at baseline was 81, decreased to 69.2 at the end of cycle 3, and was 27.9 as of Cycle 7 Day 1. This patient has continued on therapy for over 71 weeks and the disease has remained stable.

Example 3—Treatment of Nasopharygeal Cancer with an IL-1α-Specific MAb (Xilonix™)

The subject was a 47 year old Chinese male having EBV+(Epstein-Barr virus) nasopharyngeal carcinoma with the histological subtype lymphoepithelioma (old terminology) or non-keratinizing carcinoma. The subject was previously treated with cisplatin, 5-FU, radiotherapy, Taxotere® (Docetaxel), Gemzar® (Gemcitabine), Xeloda® (Capecitabine), adoptive EBV-directed T cell transfer, and Cymevene® (Ganciclovir) in combination with Gemzar® (Gemcitabine). Prior to starting therapy, the patient had fatigue, fevers and sweats, and was receiving frequent therapeutic paracentesis for ascites.

The subject began MABp1 treatment on day 0 at 1.25 mg/kg IV every two weeks. By days 3 and 4, a marked decrease in the subjects fatigue, fevers, and sweats was noted. The ascites also resolved. Abdominal CT abdomen scans showed a reduction in the size of a metastatic liver tumor from 50.4 mm on day 1 to 35.8 mm by day 36 (almost 30%) of one of the masses. Multiple other liver lesions decreased in size, and bone lesions appeared to be stable.

Example 4—Treatment of Castleman's Syndrome with an IL-1α-Specific MAb (Xilonix™)

The subject was a 55-year-old woman suffering from Castleman's disease (the variant known as POEMS syndrome). Her symptoms included fatigue, edema, and nerve pain. Prior treatment with Rituxan® (Rituximab) and an investigational anti-IL-6 therapy failed. The subject was administered a total of four infusions of MABp1 (0.75 mg/kg) every 21 days. The subject's dose was increased to 1.25 mg/kg in the next cycle.

This subject had stable disease through 2 re-stagings, and has been treated for over 4 months. For approximately 2 weeks after each injection, her symptoms of fatigue, edema, and nerve pain improved significantly, and then gradually recurred until the next injection. Her RECIST staging criteria showed 2% increase of lymph node size from baseline at the first restage, and 4% increase of lymph node size from baseline at the second restage.

After completing 7 cycles, the subject withdrew consent for therapy in order to try another experimental treatment. After being off study for 8 weeks, the subject physician requested that she be allowed to resume therapy with MABp1 due to "rapid disease progression". Since resuming treatment, the subject's disease is stable and she has been on study for over 58 weeks.

Example 5—Treatment of NSCLC with an IL-1α-Specific MAb (Xilonix™)

The subject was an 84 year old female with a history of metastatic non-small cell lung cancer diagnosed by fine needle aspiration. Three months after diagnosis, the subject began treatment with Tarceva® (Erlotinib) for 8 months at which point disease progression was noted. The subject was then treated with 11 cycles of Alimta® (Permetrexed) over 8 months, at which time treatment was halted due to the development of renal failure of undetermined etiology. Six months later, progressive disease was noted and the patient was again treated with Tarceva® (Erlotinib) for 3 months. At that point, her CAT scan showed further progressive disease in the lungs with an increase in size of a right upper-lobe mass, pulmonary nodules consistent with metastases, and increasing intra-thoracic adenopathy.

The subject was then enrolled in a trial using Xilonix™. MABp1 (3.75 mg/kg) was infused intravenously every 21 days for 9 cycles. After treatment, stable disease was noted for approximately 30 weeks, and in the most recent restaging the right lung lesion appeared to be cavitating.

Example 6—Treatment of Non-Small Cell Lung Cancer with an IL-1α-Specific MAb (Xilonix™)

The subject was a 52 yr old female diagnosed with KRAS-positive non-small cell (adenocarcinoma) cancer of the lung on day 0. A PET/CT scan from day 14 revealed a 4×3.5 cm left upper lobe mass, with disease metastasis to the lungs, hilar nodes, right inguinal nodes, right adrenal, 4th right rib, and sacroiliac joint. The subject began treatment with Carboplatin, Paclitaxel, and Bevacizumab a few weeks after the scan. The subject had a good initial response and completed five cycles before progressing at about 5 months from the first treatment. Over the next six months, the subject was treated with 3 cycles of Docetaxel and one cycle of Carboplatin plus Pemetrexed. Despite this therapy, she continued to progress.

The subject subsequently began treatment with MABp1. After only 4 days the subject began experiencing a worsening of her headaches. These were initially attributed to sinusitis, but MRI revealed brain metastases. The investigator believed that these were likely present prior to beginning therapy, however, the subject came off of study after only one dose of MABp1 to receive gamma-knife radiotherapy. The subject was seen in follow up twenty days after the initial MABp1 dose, and reported a subjective improvement in symptoms with a decrease in her chest pain. Because of this, the investigator checked a chest x-ray, which showed "an obvious decrease in the size of her lung lesions" after only one dose. A waiver was issued, and the subject resumed therapy. Forty-six days after the initial MABp1 dose, the subject underwent restaging, and had a 6% decrease in the sum total diameter of lesions as graded by RECIST criteria.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of stabilizing a progressive cancer in a human patient having cancer that has progressed after treatment with chemotherapy, radiotherapy, or biologic agents, the method comprising the step of repeatedly administering to the human patient a pharmaceutical composition comprising a pharmaceutically acceptable carrier and an anti-interleukin-1alpha (anti-IL-1α) antibody at least until the progression of the cancer has been stabilized, wherein the anti-IL-1α antibody binds human IL-1α with a Ka of at least $1 \times 10^9$ $M^{-1}$.

2. The method of claim 1, wherein the human patient's progressive cancer is metastatic, and the step of repeatedly administering the pharmaceutical composition results in a decrease in the tumor burden in the patient.

3. The method of claim 1, wherein the progressive cancer is metastatic colorectal cancer.

4. The method of claim 2, wherein the progressive cancer is metastatic colorectal cancer.

5. The method of claim 1, wherein the progressive cancer is metastatic non-small cell lung cancer.

6. The method of claim 2, wherein the progressive cancer is metastatic non-small cell lung cancer.

7. The method of claim 1, wherein the anti-IL-1α antibody is a monoclonal antibody (mAb).

8. The method of claim 7, wherein the mAb is an IgG1.

9. A method of stabilizing a progressive cancer in a human patient having cancer that has progressed after treatment with chemotherapy, radiotherapy, or biologic agents, the method comprising the step of repeatedly administering to the human patient a pharmaceutical composition comprising a pharmaceutically acceptable carrier and an anti-interleukin-1alpha (anti-IL-1α) antibody at least until the progression of the cancer has been stabilized, wherein the anti-IL-1α antibody is not conjugated to a radionuclide, and wherein the anti-IL-1α antibody is an IgG1 and binds human IL-1α with a Ka of at least $1 \times 10^9$ M$^{+}$1.

10. The method of claim 9, wherein the human patient's progressive cancer is metastatic, and the step of repeatedly administering the pharmaceutical composition results in a decrease in the tumor burden in the patient.

11. The method of claim 9, wherein the progressive cancer is selected from the group consisting of colorectal cancer, non-small cell lung cancer, metastatic colorectal cancer, and metastatic non-small cell lung cancer.

12. The method of claim 9, wherein the anti-IL-1α antibody is a monoclonal antibody (mAb).

* * * * *